United States Patent [19]

Haughton

[11] Patent Number: 4,864,851
[45] Date of Patent: Sep. 12, 1989

[54] SENSOR AND SYSTEM FOR CONTINUOUS DETERMINATION OF SHEET STRENGTH

[75] Inventor: Paul J. Haughton, Los Gatos, Calif.

[73] Assignee: Measurex Corporation, Cupertino, Calif.

[21] Appl. No.: 56,332

[22] Filed: May 26, 1987

Related U.S. Application Data

[63] Continuation of Ser. No. 784,213, Oct. 4, 1985, abandoned, and a continuation-in-part of Ser. No. 730,406, May 2, 1985.

[51] Int. Cl.$^4$ .............................................. G01L 5/04
[52] U.S. Cl. ..................................... 73/159; 162/263
[58] Field of Search ................... 73/159, 11, 769, 773, 73/774, 781, 785, 788, 794, 804, 838, 81, 78, 82, 85; 162/263, 49; 364/471

[56] References Cited

U.S. PATENT DOCUMENTS

| | | | |
|---|---|---|---|
| 2,809,519 | 10/1957 | Kaestner | 73/159 |
| 2,826,911 | 3/1958 | Hartford et al. | 73/159 |
| 2,834,203 | 5/1958 | Sampson | 73/81 |
| 2,966,791 | 1/1961 | Di Pieri | |
| 3,474,668 | 10/1969 | Morgan | 73/159 |
| 3,718,037 | 2/1973 | Stringer et al. | |
| 3,738,151 | 6/1973 | Giunta et al. | 73/1 B |
| 3,793,878 | 2/1974 | Brunton | 73/785 |
| 4,068,385 | 1/1978 | Mitzel | 73/159 |
| 4,291,577 | 9/1981 | Baum et al. | 73/597 |
| 4,453,404 | 6/1984 | Powell et al. | 73/159 |

FOREIGN PATENT DOCUMENTS

| | | |
|---|---|---|
| 751614 | 10/1954 | Fed. Rep. of Germany . |
| 1008503 | 5/1957 | Fed. Rep. of Germany ........ 73/159 |
| 1012760 | 7/1957 | Fed. Rep. of Germany ........ 73/159 |
| 2054505 | 11/1969 | Fed. Rep. of Germany ........ 73/159 |
| 475609 | 6/1979 | Switzerland . |
| 934328 | 8/1963 | United Kingdom .................. 73/159 |
| 1328158 | 8/1973 | United Kingdom .................. 73/159 |

OTHER PUBLICATIONS

Foxboro Bulletin, Aug. 1964.
A High Temperature Four-Point Bending Machine for Testing Thin Sheets of Refractory Materials, J. L. Martin, R. Case, A. Devacht and P. Costa, Office National d'Etudes et de Recherches Aerospatiales, 12/29/70.

Primary Examiner—Michael J. Tokar
Assistant Examiner—Robert R. Raevis
Attorney, Agent, or Firm—Spensley Horn Jubas & Lubitz

[57] ABSTRACT

A sensor for sensing a quality of paper related to elastic modulus and bending stiffness as it is being made including a paper support in the form of a ring and a free running wheel, which depresses the paper in the center of the ring as the paper passes over it. A force transducer mounted to the wheel senses the force of the deflected paper on the wheel and provides a measure of a characteristics of the paper related to its elastic modulus and bending stiffness. This factor, together with basis weight, thickness and paper velocity are used to determine the strength of the paper on a continuous basis.

40 Claims, 3 Drawing Sheets

SENSOR AND SYSTEM FOR CONTINUOUS DETERMINATION OF SHEET STRENGTH

This is a continuation of copending application Ser. No. 784,213, filed on Oct. 4, 1985, now abandoned and also a continuation-in-part of copending application Ser. No. 730,406, filed on May 2, 1985.

BACKGROUND OF THE INVENTION

One of the critical parameters involved in the manufacture of paper is its strength. Virtually all paper manufactured is sold with a strength specification of some sort, but up to the present time it has not been practical to accurately measure the strength of paper "on line" as it is being manufactured. Since paper making is a high speed continuous process, large amounts of paper can easily be produced before the strength of the paper made can be confirmed by subsequent measurement.

Strength specifications for paper are usually given in terms of an empirical destructive test, one of the more common of these being the "burst pressure" or "Mullen" test. A burst pressure test is conducted by clamping a sample of the paper between two circular clamping rings having a specified standard inside diameter, and building up pressure on one side of the paper until the paper bursts (using a rubber diaphragm and liquid pressure). The pressure required to burst the paper is known as the "burst pressure" and is the figure often used to specify the required strength.

Needless to say, the burst pressure test does not lend itself for use in connection with the continuous measurement of paper strength. Because of its widespread popularity, however, any other method used to measure the strength of paper should provide results which correlate with the standard burst pressure test.

SUMMARY OF THE INVENTION

Accordingly, it is an object of the present invention to provide an "on line" continuous measurement of paper strength. By its nature, a measurement of strength is destructive. Fortunately, however, the strength of paper has been found to be related to factors which are known, or can be measured on a continuous basis. The factors which have been identified as affecting the strenght are the "elastic modulus" of the paper, its basis weight and its thickness. Quotation marks are used around the term "elastic modulus" to indicate that the function, while related to the elastic modulus is really an empirically derived factor which depends on other characteristics also. The most important secondary factor involved is the bending stiffness of the sheet. In any particular paper making set up, changing the speed of the web also affects the strength of the resulting product.

Elastic modulus and bending stiffness are difficult, if not impossible to measure directly on a moving web of paper. However, a sensor has been developed which senses a physical manifestation of the paper related to these characteristics and provides an output which, when taken together with the other aforementioned factors, can be used to determine paper strength. An empirical equation relating these factors with strength has been developed.

A clear understanding of the invention can be had by referring to the following detailed description of the presently preferred embodiment of the invention together with the appended drawings.

DETAILED DESCRIPTION OF THE INVENTION

Paper is ordinarily made in a continuous sheet by high speed machines, often several hundred feet in length. The process involves laying a wet mass of wood pulp onto a moving wire fabric belt, drying the mass, and finally calendering the sheet to give it the desired surface finish. The present invention is most advantageously used to monitor the strength of the paper after the final calendering operation, and before the paper is rolled up on the final reel. A reroll motor (not shown) maintains a constant tension in the sheet between the calender and the reroll reel. Since the strength of the paper produced may vary across the sheet as well as along the sheet, the present invention preferably involves the use of a scanning system whereby the sensors scan across the width of the paper while the paper is being fed out of the calender and into the reroll system.

Figure 1:
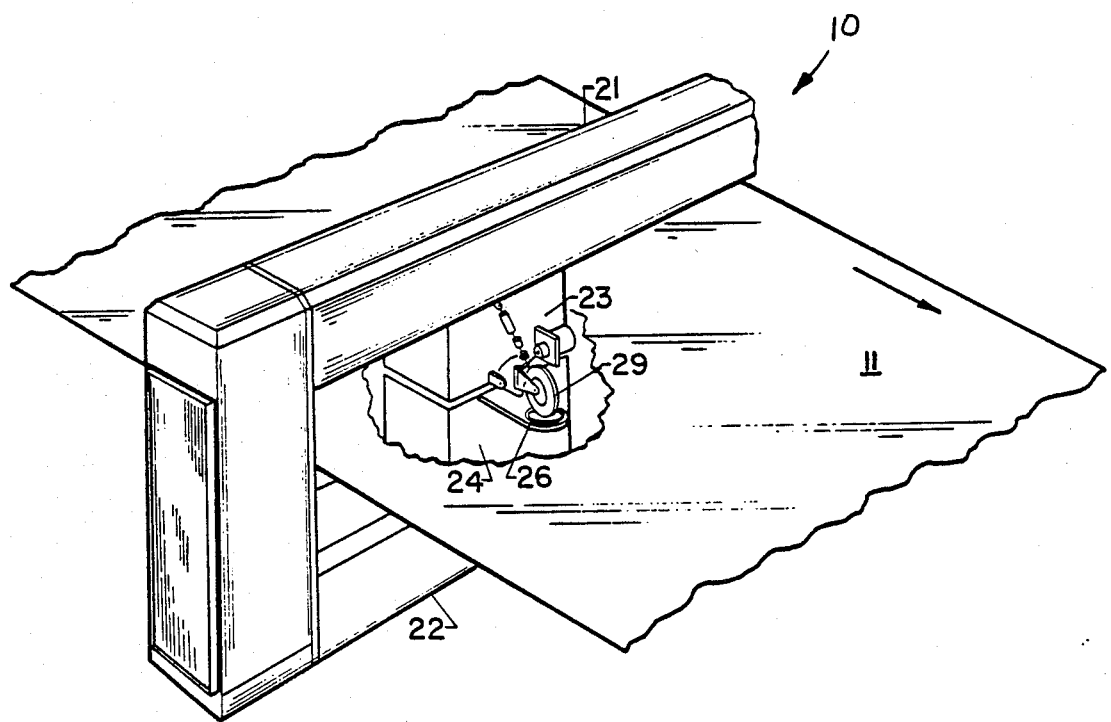
FIG. 1 is a perspective view of the sensing portion of the invented apparatus as installed in a paper making machine.
Figure 6:
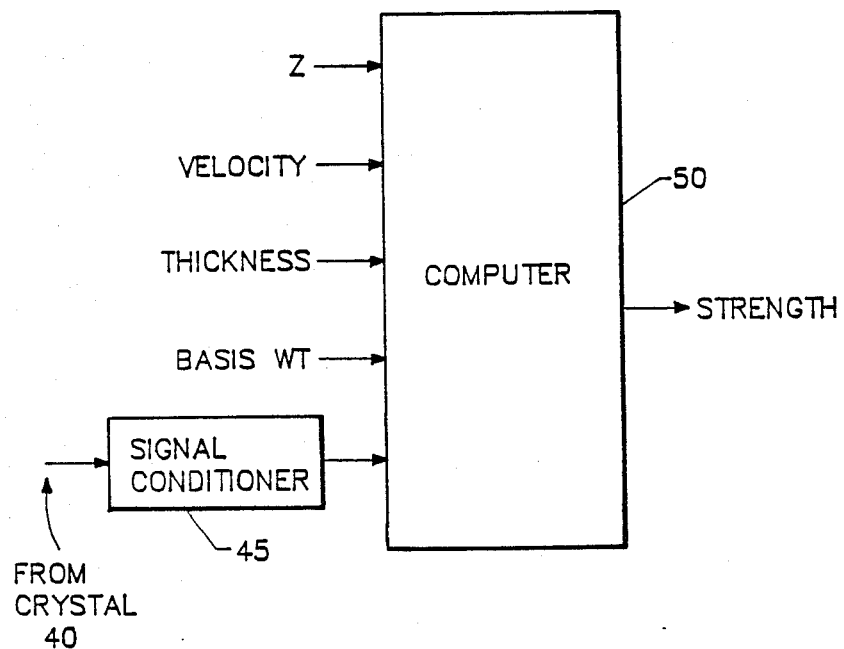
FIG. 6 is a block diagram of the electronic portion of the invention.

FIG. 1 shows a scanning station 10 which, as noted above, is preferably located after the final calender rolls. A web of paper 11, which is driven by rotation of rolls 5, 7, can be seen passing through the scanning station between two transverse beams 21 and 22 on which are mounted upper and lower gage support members 23 and 24. The web paper 11 in FIG. 1 is shown with cut out area so that the relationship between the gage support members can be seen. A motor within the scanning station is coupled to, and drives the gage support members 23, 24 back and forth across the width of the paper in a continuous scanning motion, keeping them in alignment at all times.

The gage support members carry four sets of sensors which provide the data used to calculate paper strength. The four factors used are basis weight, thickness, "elastic modulus", and the velocity of the web. Means for determining basis weight, thickness, and paper velocity are all known in the prior art and are therefore not shown or discussed herein. Thickness and paper velocity are relatively simple to measure, and many methods are known in the prior art. Basis weight is a more complex matter, but a suitable method is disclosed in U.S. Pat. No. 3,757,122 issued to Bossen et al. The fourth sensor provides data which relates to the "elastic modulus" of the paper. As noted above, the sensor is responsive not only to the elastic modulus of the sheet, but also to its stiffness in bending.

Figure 2:
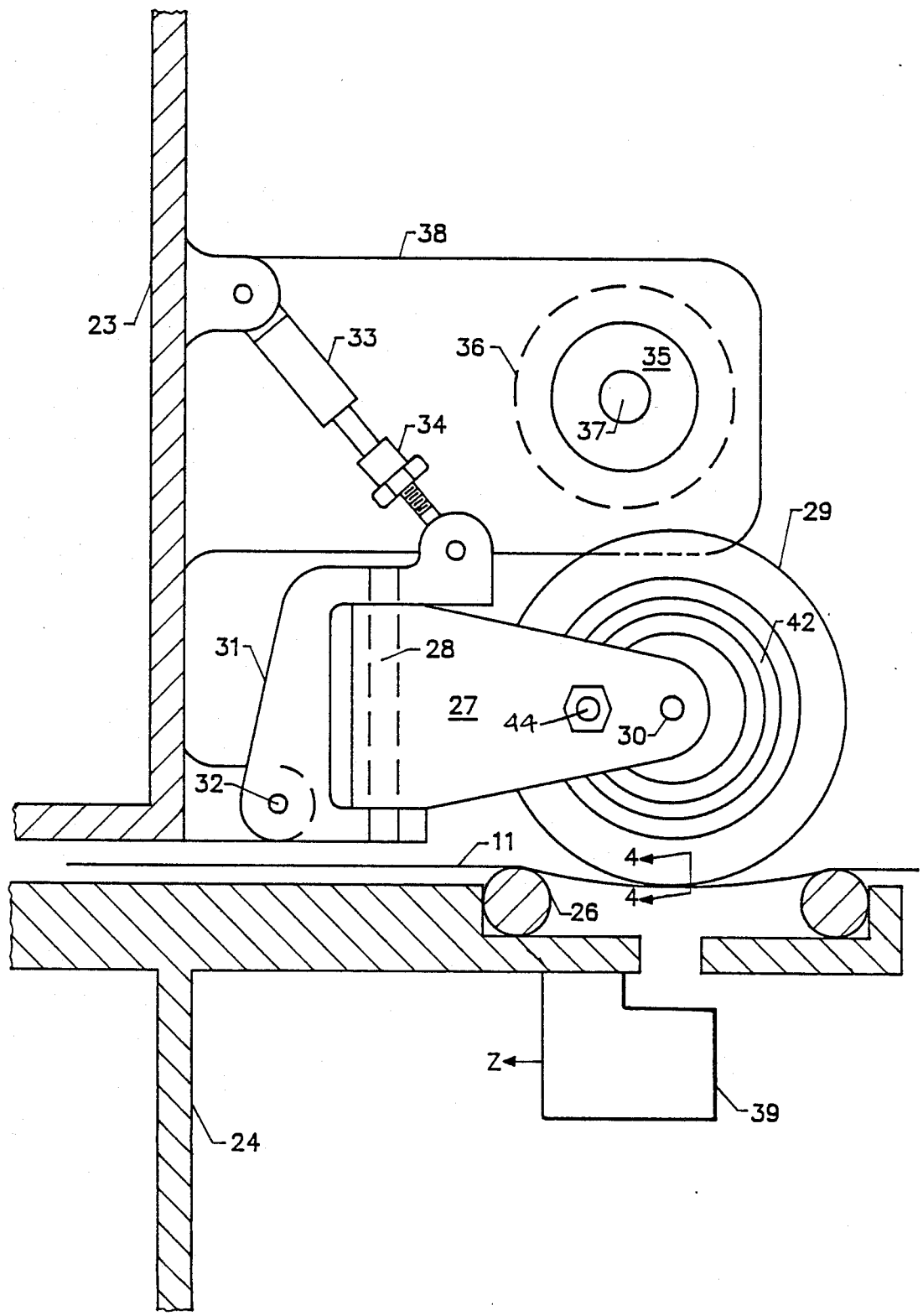
FIG. 2 is a partly cross sectional side view of the sensor for sensing the "elastic modulus" of the paper.

FIG. 2 shows a partially sectioned side view of the invented "elastic modulus" sensor. Lower gage support 24 supports a horizontal ring 26 whose top surface is preferably aligned with the paper web 11. While a ring such as ring 26 is the preferred method of support, other forms of supporting structure could be used which support the paper in the vicinity of a central region.

Upper gage support 23 carries the sensing wheel assembly which comprises bracket 31, yoke 27 and wheel 29. Pins 28 and 32 allow the wheel freedom to move both horizontally and also up and down while bearings on axle 30 (not shown) permit the wheel to rotate freely. Up and down motion of the wheel 29 is controlled by air cylinder 33. In its extended position, air cylinder 33 positions the lower portion of the periphery of wheel 29 a fixed distance below the top surface of ring 26. For purposes of example, and not by way of limitation, if the diameters of wheel 29 and ring 26 are each about 5 inches, a satisfactory position for the lowest point on wheel 29 may be ¼ inch below the top surface of ring 26. When the air cylinder 33 is retracted, wheel 29 will be in contact the rubber covered wheel 35. Stop 34 adjusts the upper position of wheel 29 so as to set the force exerted by the rubber on wheel 29. The purpose of this arrangement will be discussed below.

Inset in wheel 29 are a piezoelectric dynamic force transducer 40 and contact button 41. The outer surface of contact button 41 conforms to the surface of the wheel 29. A force on contact button 41 will compress the piezoelectric transducer 40 so as to generate a voltage between its faces. This voltage is conducted by a pair of wires to slip rings 42 and 43 and thence through a pair of brushes 44 (only one of which can be seen in the drawings) to signal conditioner 45.

Figure 5:
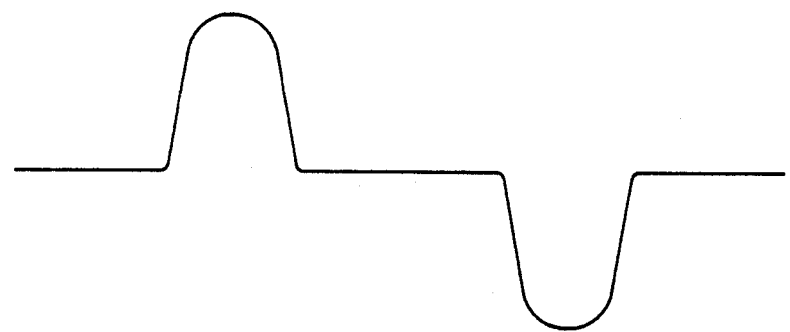
FIG. 5 shows the waveform of the signal produced by the sensor of FIG. 2.

Each time button 41 contacts the paper web, a pair of voltage pulses are generated as shown in FIG. 5. The positive pulse generated when the button contacts the paper is used to trigger a gate in the signal conditioner 45 so that the signal conditioning circuitry will be in a condition to accept the negative pulse which follows.

The purpose of gating the negative pulse is to reduce the effect of any electrical noise in the system. The negative pulse is integrated in signal conditioner 45, as is common practice with piezoelectric transducer signals. Since the voltage output of a piezoelectric crystal is proportional to the rate of change of the force applied between its faces, the magnitude of the integrated negative pulse is proportional to the force of the paper web on the contact button.

Figure 4:
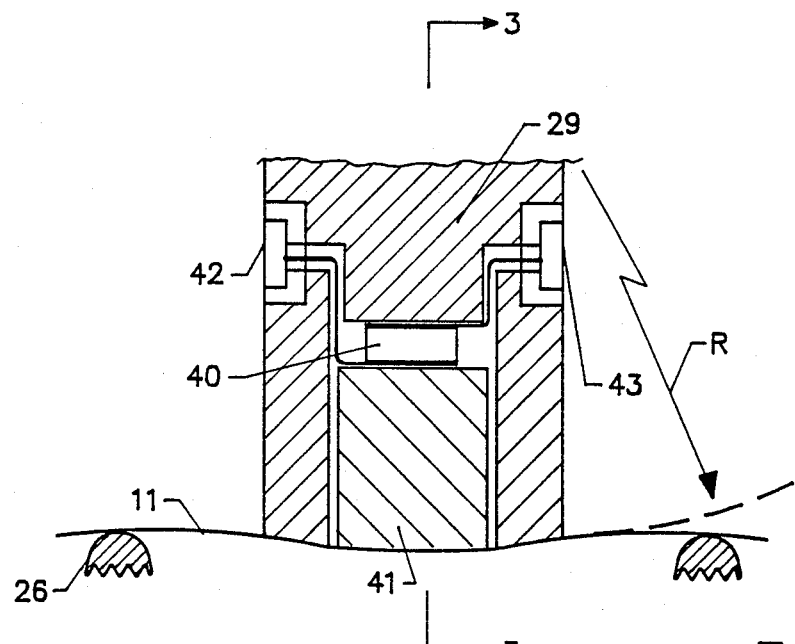
FIG. 4 is a fragmentary cross sectional view of the sensing wheel of FIG. 2 taken at 4—4 of FIG. 2.
Figure 3:
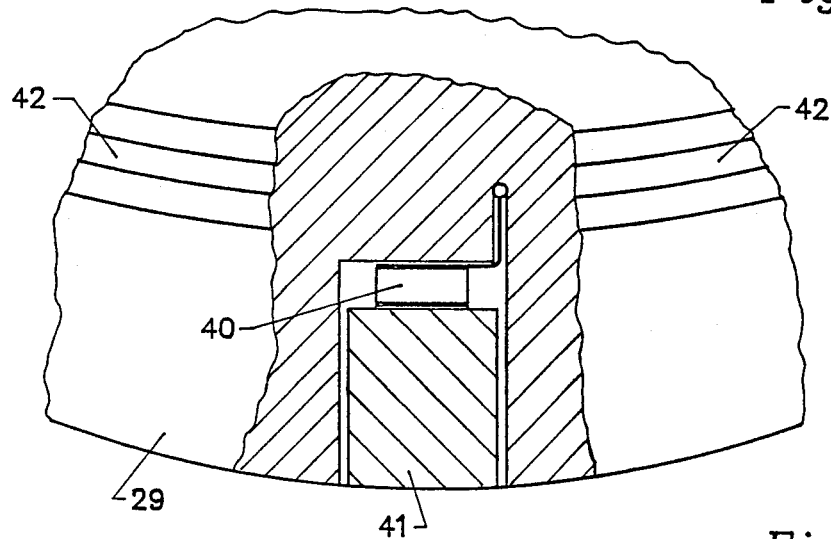
FIG. 3 is a partial side view, partly cross sectioned, of the sensing wheel of the sensor of FIG. 2.

The periphery of wheel 29 is not cylindrical but, rather, is preferably approximately spherical. That is, the radius R as shown in FIG. 4 is preferably approximately equal to one half the wheel diameter. The wheel surface need not be spherical, but is preferably at least convex, particularly if a load sensor as utilized in the preferred embodiment disclosed herein is used. The force exerted by the paper on the wheel is a function of several factors including the tension on the sheet, the elastic modulus of the paper, the bending stiffness of the paper, and the physical dimensions of the gaging components.

The output of signal conditioner 45 (the integrated negative voltage pulse from piezoelectric crystal 40) is coupled to computer 50 where it is combined with signals from the other sensors to arrive at a value for the strength of the paper. An empirical equation has been developed which provides a strength determination which correlates well with the standard "Mullen" test. This equation is:

$$S = A \times \frac{L}{Lav} + (B \times W^E \times T^F) - C \times V^D \quad (1)$$

where
S is the strength of the paper,
A,B,C,D,E and F are constants,
L is the force of the paper on button 41 (the integrated negative pulse output of crystal 40),
Lav is the average value of L over the width of the paper,
W is the basis weight of the paper,
T is the thickness of the paper, and
V is the velocity of the paper web leaving the calender.

The above equation has been found to be applicable to a wide variety of papers being manufactured. The constants A, B, C, D, E and F vary somewhat depending on the particular paper being made, but generally fall within the following ranges (where basis weight is in pounds per 1000 square feet, thickness is in mills, and velocity is in feet per minute):

A from 20 to 22
B from 0.5 to 5
C from 0 to 0.07
D from 0.5 to 5
E from 1 to 2
F from −1 to +1

The following table lists several specific cases by way of example. The samples listed are all kraft paper to various grades.

| SAMPLE NO. | S (#/IN$^2$) | W (#/MFT$^2$) | T (MILS) | V (FT/MIN) | A | B | C | D | E | F |
|---|---|---|---|---|---|---|---|---|---|---|
| 1 | 83.58 | 32.5 | 10.9 | 1630 | 21 | 1.03 | $8.4 \times 10^{-7}$ | 2.30 | 1.57 | −.45 |
| 2 | 60.50 | 26.0 | 8.4 | 2095 | 21 | 1.03 | $7.0 \times 10^{-1}$ | .476 | 1.57 | −.45 |
| 3 | 54.74 | 22.8 | 8.3 | 2300 | 21 | 1.03 | $1.42 \times 10^{-16}$ | 5.10 | 1.57 | −.45 |
| 4 | 43.80 | 19.7 | 6.7 | 1849 | 21 | 1.03 | $1.23 \times 10^{-12}$ | 4.07 | 1.57 | −.45 |

In all of the above cases, the tension on the sheet was kept at a constant value of 60 pounds per linear inch of width of the paper. Lav for the various samples (in arbitrary units) varied from about 3 to 4.5, and the variation in L across the width of the sheet was in all cases of the order of ±20%. As can be seen, the factor $CV^D$ in some cases can be relatively small compared to the other factors in the equation, and in those cases could be neglected or replaced with a constant with relatively small loss in accuracy. It also may be noted that the force on the wheel 29 appears only as L/Lav. This indicates that the "elastic modulus" is primarily an indicator of how the paper strength varies across the width of the paper, while the average strength is primarily determined as a function of basis weight and thickness.

The above data presupposes that the lowest point on the periphery of wheel 29 is maintained at a constant distance below the top surface of ring 26. If the mechanical rigidity of the structure is such that the spacing cannot be maintained, sensing means can easily be adapted to sense the relative positions of wheel 29 and ring 26, and to apply a correction to the L/Lav term to account for variations. A conventional sensor for this purpose is shown diagrammatically in FIG. 2 identified by the numeral 39. The output of displacement sensor 39 is designated as "Z" and is used to modify to L/Lav term of equation (1) as a multiplier, viz. f(Z)×L/Lav.

It has been found desirable to standarize the output of signal conditioner 45 from time to time. By retracting air cylinder 33 until stop 34 rests against the cylinder, wheel 29 is raised out of contact with the paper web and into contact with wheel 35. Wheel 35 is made of a rubberlike material and is driven with a surface speed approximately that of web 11 by motor 36 through shaft 37. The hardness of wheel 35 is selected so that the force on crystal 40 will be in the range experienced by the crystal when it is bearing against a paper web. By running the sensor in the standardizing position, the output of the "elastic modulus" sensor can be standardized, and the whole system set up without running the paper making machine.

What has been described is a novel sensor and system for determining paper strength "on line". A presently preferred embodiment has been disclosed for purposes of illustration, but it will be understood that persons skilled in the art will be able to make changes thereto within the spirit of the invention and therefore the scope of the invention should be limited only by the following claims.

I claim:

1. A sensor for non-destructively sensing the failure strength of a moving sheet of material travelling under tension, wherein the sheet of material has a width in the plane of the sheet perpendicular to the direction of travel, the sensor comprising:
   (a) supporting means for supporting said travelling sheet at a plurality of points defining an unsupported area within said plurality of points;
   (b) a free running wheel supported to have its periphery in contact with said sheet of material to deflect the sheet into said unsupported area;
   (c) a force transducer mounted for rotation with the wheel for sensing the force exerted on said free running wheel by said travelling sheet of material and producing a signal indicative of the sensed force; and
   (d) computing means for receiving the force signal and determining the failure strength of the sheet based upon the signal.

2. A sensor as recited in claim 1 wherein said supporting means is a ring surrounding said unsupported area.

3. A sensor as recited in claim 1 wherein the free running wheel has a periphery which is convex and wherein said force transducer comprises a force collecting member and a piezoelectric crystal mounted to said wheel.

4. A sensor as recited in claim 3 wherein the periphery of said wheel is spherical.

5. A sensor as recited in claims 1, 2, 3, or 4 and further including means for moving said sensor, except said computing means, across the width of said moving sheet in a continuous scanning motion.

6. A sensor as recited in claims 1, 2, 3, or 4 and further including standardizing means comprising:
   (a) a motor;
   (b) a compressible wheel attached to the shaft of said motor; and
   (c) means for bringing the periphery of said free running wheel into contact with said compressible wheel.

7. A system for nondestructively detecting the failure strength of a travelling sheet of paper wherein the sheet of paper has a width in the plane of the sheet perpendicular to the direction of travel, the system comprising:
   (a) means for detecting one or more selected variables related to the failure strength of said sheet of paper and for providing an output signal related thereto;
   (b) means for detecting a physical characteristic of said sheet of paper and for providing an output signal related thereto comprising:
      (i) support means for supporting said sheet at a plurality of points defining a central unsupported area within said plurality of points;
      (ii) a free running member supported to have its periphery in contact with said sheet of paper in said unsupported area;
      (iii) a force transducer for sensing the load exerted on the free running member by said travelling sheet; and
   (c) computer means for calculating the failure strength of said travelling sheet of paper as a function of the output signals from the means for detecting said selected variables and the means for detecting a physical characteristic.

8. A system as recited in claim 7, further comprising means for moving said means for detecting a physical characteristic across the width of said travelling sheet in a scanning motion.

9. A system as recited in claim 8 wherein the function utilized by the computer means in its strength calculation is:

$$S = A \times \frac{L}{L_{av}} + (B \times W^E \times T^F)$$

where
S is the failure strength of said sheet,
A, B, E and F are constants,
L is the instantaneous force applied to said force transducer,
$L_{av}$ is the average force applied to said force transducer over the width of said sheet,
W is the basis weight of said sheet, and
T is the thickness of said sheet and wherein said means for detecting the selected variables includes means for detecting basis weight and thickness of said sheet and for providing output signals related thereto.

10. A system as recited in claim 9 where, if W is stated in pounds per thousand square feet and T is states in mils, A is between 20 and 33, B is between 0.5 and 5, E is between 1 and 2, and F is between −1 and +1.

11. A system as recited in claim 8 further including means for detecting the velocity of said traveling sheet of paper and for providing an output signal related thereto, and wherein the function utilized by the computer means includes said output signal related to said detected velocity of said travelling sheet of paper.

12. A system as recited in claim 11 wherein the function utilized by the computer means is:

$$S = A \times \frac{L}{L_{av}} + (B \times W^E \times T^F) + C \times V^D \text{ where}$$

S is the failure strength of said sheet,
A, B, C, D, E and F are constants,
L is the instantaneous force applied to said force transducer, $L_{av}$ is the average force applied to said force transducer over the width of said sheets,
W is the basis weight of said sheet,
T is the thickness of said sheet, and
V is the velocity of said sheet.

13. A system as recited in claim 12 where, if W is stated in pounds per thousand square feet, T is stated in mils, and V is stated in feet per minute, A is between 20 and 22, B is between 0.5 and 5, C is between 0 and 0.07, D is between 0.5 and 5, E is between 1 and 2, and F is between −1 and +1.

14. A system as recited in claims 8, 9, 10, 11, 12 or 13 wherein said free running member is a wheel and the force transducer is mounted to the periphery of said wheel, and further including
means for sensing the relative displacement between said free running wheel and said support means supporting said sheet and for providing an output indicative of the sensed relative displacement, and
means for altering the strength calculation of said computer means responsive to the output of said means for sensing said relative displacement.

15. A sensor for sensing the failure strength of a travelling sheet of material under tension which comprises:
 (a) support means for supporting said travelling sheet of material at a plurality of points defining an unsupported area between the points;
 (b) contact means for deflecting said travelling sheet of material into said unsupported area;
 (c) force means for providing a first electrical signal responsive to the force acting between said travelling sheet and said contact means;
 (d) displacement means for providing a second electrical signal indicative of the displacement of the support means relative to the contact means; and
 (e) computing means for determining the failure strength of the sheet based upon the first electrical signal from the force means and the second electrical signal from the displacement means.

16. A sensor as recited in claim 15 where said plurality of points defines a substantially circular central unsupported area.

17. A sensor as recited in claim 15 wherein said contact means comprises a free running wheel.

18. A sensor as in claim 15, further comprising means for maintaining the travelling sheet under substantially constant tension.

19. A method for determining the failure strength of a sheet of material travelling under tension, wherein the sheet of material has a width in the plane of the sheet perpendicular to the direction of travel, said method comprising:
 (a) supporting said sheet at a plurality of points by a support means defining an unsupported area between the points;
 (b) contacting said sheet with a free running wheel to forceably deflect said sheet into said unsupported area;
 (c) sensing the amount of force exert between said free running wheel and said support means with a force transducer mounted for rotation with the wheel; and
 (d) determining the failure strength of the sheet based upon the sensed force.

20. A method for nondestructively determining the failure strength of a travelling sheet of paper, the sheet having a width in the plane of the sheet perpendicular to the direction of travel, the method comprising:
 (a) detecting the basis weight of said sheet;
 (b) detecting the thickness of said sheet;
 (c) supporting said sheet at a plurality of points by support means defining an unsupported area between said points;
 (d) contacting said sheet with a contacting means to force said sheet into said unsupported area;
 (e) sensing the relative force between said support means and said contacting means; and
 (f) computing the failure strength of said sheet as a function of detected basis weight, detected thickness, and said sensed relative force.

21. A method as recited in claim 20, further comprising the step of cooperatively moving the support means and the contacting means across the width of said sheet in a scanning motion.

22. A method as recited in claim 21, wherein said computing step comprises computing a value of S using the function:

$$S = A \times \frac{L}{L_{av}} + (B \times W^E \times T^F) \text{ where}$$

S is the failure strength of said sheet,
A, B, E and F are constants,
L is the instantaneous value of said sensed force,
$L_{av}$ is the average value of said sensed force over the width of said sheet,
W is the detected basis weight of said sheet, and
T is the detected thickness of said sheet.

23. A method as recited in claim 21 further including the step of detecting the velocity of said sheet, wherein the computing step utilizes the detected velocity in computing the failure strength of said sheet.

24. A method as recited in claim 23 wherein said computing step comprises computing values of S utilizing the function:

$$S = A \times \frac{L}{L_{av}} + (B \times W^E \times T^F) + C \times V^D$$

where
S is the failure strength of said sheet,
A, B, C, D, E and F are constants,
L is the instantaneous value of said sensed force,
$L_{av}$ is the average value of said sensed force over the width of said sheet,
W is the basis weight of said sheet,
T is the detected thickness of said sheet, and
V is the detected velocity of said sheet.

25. A method as recited in claim 21 further including the steps of sensing the relative displacement between said contacting means and said support means, and altering said computing step to compensate for changes in said relative displacement.

26. A sensor for non-destructively sensing a physical characteristic of a travelling sheet of paper moving under tension between a first and a second sheet support, the sheet having a width in the plane of the sheet perpendicular to the direction of travel, the sensor comprising:
 (a) on one side of the sheet between the first and the second sheet supports, a support ring mounted approximately coplanar with, and in close proximity to, a surface of the sheet for supporting the sheet around an unsupported area, the diameter of the ring being substantially smaller than the width of the sheet;

(b) on the other side of the sheet between the first and second sheet supports, a rotating wheel for displacing the sheet into said unsupported area;

(c) a force transducer mounted to the periphery of the wheel for rotation with the wheel to detect the amount of force between the wheel and the sheet of paper supported by the ring; and (d) means for controllably moving the ring and wheel across the width of the travelling sheet.

27. A system for detecting the failure strength of a sheet of paper travelling in tension between a first and a second sheet support, the sheet having a width in the plane of the sheet perpendicular to the direction of travel, the system comprising:

(a) sensor means for non-destructively detecting a physical characteristic of the travelling sheet, the sensor means including:

(i) support means mounted to support one side of the sheet, the support means defining a relatively small unsupported area of the sheet between the first and second sheet supports;

(ii) displacement means mounted on the opposite side of the sheet to displace the sheet within said unsupported area; and (iii) force transducing means for detecting the force exerted to displace the sheet into the unsupported area and for providing a first signal indicative of the detected force;

(b) scanning means to move the sensor means across the width of the travelling sheet;

(c) position sensing means for detecting, relative to said support means, changes in the displacement of the sheet by said displacement means, and for providing a second signal indicative of said relative displacements; and (d) computer means for receiving the signals from the sensor means and the position sensing means, and for calculating the failure strength of the sheet along a profile across the width of the sheet employing said first and second signals.

28. A system as in claim 27, further comprising means for maintaining the travelling sheet under substantially constant tension.

29. A system for determining the failure strength of a moving sheet of material, comprising:

(a) support means for supporting the moving sheet at a plurality of points defining an unsupported area between said points;

(b) a deflecting member having a sheet deflecting surface disposed to deflect said moving sheet into said unsupported area;

(c) displacement sensor means for providing a displacement signal indicative of the distance the sheet is deflected by said deflecting member; and (d) computing means for computing the failure strength of said sheet based upon the displacement signal.

30. A system as in claim 29, further comprising means for maintaining the moving sheet under substantially constant tension.

31. A system for sensing a physical characteristic of a moving sheet of material, said sheet having a width in the plane of the sheet perpendicular to the direction of sheet motion, comprising:

(a) a sensor including i. support means for supporting said moving sheet at a plurality of points defining an unsupported area within said plurality of points;

ii. a member in contact with the sheet of material for deflecting the sheet into the unsupported area; and iii. a force transducer for sensing the force exerted on the member by the moving sheet, and for generating a signal indicative of said force; and (b) means for moving the member across the width of the sheet.

32. A system as in claim 31, further comprising computing means for receiving the force signal and computing the sheet failure strength based upon said force signal.

33. A system as in claim 31 having only a single sensor.

34. A system for sensing a physical characteristic of a moving sheet, said sheet having a width in the plane of the sheet perpendicular to the direction of sheet motion, comprising:

a single sensor including (i) support means for supporting said moving sheet at a plurality of points defining an unsupported area between said plurality of points;

(ii) a member disposed for contact with the moving sheet of material to deflect the sheet into the unsupported area, the dimension of the area of contact of the member with the sheet along the width of the sheet being substantially smaller than the sheet width; and (iii) a force transducer, operatively coupled to the member, for sensing the force exerted on the member by the moving shet, and for generating a signal indicative of said force.

35. A system as in claim 29, further comprising computing means for receiving the force signal and computing the sheet failure strength based upon said force signal.

36. A sheet failure strength sensor, comprising:

at least one sheet support having a sheet supporting surface and defining an open space within the at least one sheet support;

a rotatable wheel disposed with a portion of the wheel periphery within the open space;

a force transducer mounted to rotate with the wheel, the transducer being disposed to generate signals indicative of a force applied to the periphery of the wheel; and a computer, operatively coupled to the force transducer, to receive the signals and compute sheet failure strength based upon the signals.

37. A sheet failure strength sensor, comprising:

at least one sheet support having a sheet supporting surface and defining an open space within the at least one sheet support;

a sheet deflecting member disposed at least partially within the open space, the member having a sheet deflecting surface to deflect a sheet, supported by the sheet supporting surface, into the open space;

a deflection sensor, operatively coupled to the at least one sheet support and to the sheet deflecting member, to generate signals indicative of the distance between the sheet supporting surface and the sheet deflecting surface; and a computer, operatively coupled to the deflection sensor, to receive the signals and compute sheet failure strength based upon the signals.

38. A method for determining the failure strength of a sheet of material traveling under tension, wherein the sheet of material has a width in the plane of the sheet perpendicular to the direction of travel, said method comprising the steps of:
   (a) supporting said sheet at a plurality of points by a ring mounted to create an unsupported area within the ring;
   (b) contacting said sheet with a free-running wheel to forcibly deflect said sheet into said unsupported area;
   (c) sensing the amount of force exerted between said free-running wheel and said ring with a force transducer mounted for rotation with the wheel; and
   (d) determining the failure strength of the sheet based upon the sensed force.

39. A method for determining the failure strength of a sheet of a material traveling under tension, wherein the sheet of material has a width in the plane of the sheet perpendicular to the direction of travel, said method comprising the steps of:
   (a) supporting said sheet at a plurality of points by a support means defining an unsupported area between the points;
   (b) contacting said sheet with a free-running wheel to forcibly deflect said sheet into said unsupported area;
   (c) sensing the amount of force exerted between said free-running wheel and said support means with a force transducer mounted for rotation with the wheel;
   (d) moving the force transducer across the width of the traveling sheet in a scanning motion; and
   (e) determining the failure strength of the sheet based upon the sensed force.

40. A system as claimed in claim 34, wherein the support means is adapted to support the moving sheet at two points disposed on opposite sides of the unsupported area on a line oriented in a direction perpendicular to the direction of motion of the sheet.

* * * * *